(12) United States Patent
Drummond et al.

(10) Patent No.: US 7,806,226 B2
(45) Date of Patent: Oct. 5, 2010

(54) STETHOSCOPE WITH FRICTIONAL NOISE REDUCTION

(75) Inventors: Thomas E. Drummond, Stillwater, MN (US); Hatim M. Carim, West St. Paul, MN (US); Craig D. Oster, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 17 days.

(21) Appl. No.: 11/722,529

(22) PCT Filed: Dec. 21, 2005

(86) PCT No.: PCT/US2005/046520

§ 371 (c)(1),
(2), (4) Date: Jun. 22, 2007

(87) PCT Pub. No.: WO2006/073854

PCT Pub. Date: Jul. 13, 2006

(65) Prior Publication Data

US 2008/0093157 A1    Apr. 24, 2008

Related U.S. Application Data

(60) Provisional application No. 60/640,497, filed on Dec. 30, 2004.

(51) Int. Cl.
| | |
|---|---|
| *A61B 7/02* | (2006.01) |
| *A61B 7/04* | (2006.01) |
| *A61B 7/00* | (2006.01) |
| *A61B 5/02* | (2006.01) |
| *A61B 5/00* | (2006.01) |

(52) U.S. Cl. .......................... 181/131; 381/67; 600/528

(58) Field of Classification Search ................. 181/131; 600/528; 381/67
See application file for complete search history.

(56) References Cited

U.S. PATENT DOCUMENTS

| | | | | |
|---|---|---|---|---|
| 3,233,041 | A | * 2/1966 | Croslin | .......................... 381/67 |
| 3,276,536 | A | 10/1966 | Littmann | |
| 3,470,975 | A | * 10/1969 | Haiken | ....................... 181/131 |
| 4,012,604 | A | * 3/1977 | Speidel | ....................... 367/180 |
| 4,461,368 | A | * 7/1984 | Plourde | ....................... 181/131 |

(Continued)

FOREIGN PATENT DOCUMENTS

EP    0 434 310 A    6/1991

(Continued)

OTHER PUBLICATIONS

ASTM D 1894—Standard Test Method for Static and Kinetic Coefficients of Friction of Plastic Film and Sheeting.

*Primary Examiner*—Edgardo San Martin
(74) *Attorney, Agent, or Firm*—Daniel R. Pastirik; Nancy M. Lambert; Nicole J. Einerson

(57) ABSTRACT

A stethoscope is provided, comprising: a sound receiving member (12) for receiving sounds, the sound receiving member capable of transmitting sound received thereby; a head set coupled to the sound receiving member to receive sound transmitted by the sound receiving member; means for reducing frictional noise, said means associated with the sound receiving member to reduce noise caused by relative movement between a surface and the sound receiving member of the chestpiece in contact with the surface.

15 Claims, 5 Drawing Sheets

U.S. PATENT DOCUMENTS

| | | | |
|---|---|---|---|
| 4,598,590 A | 7/1986 | Busch-Vishniac et al. | |
| 4,770,270 A | 9/1988 | Grimm | |
| 4,852,684 A | 8/1989 | Packard | |
| 4,903,794 A * | 2/1990 | Klippert et al. | 181/131 |
| 4,913,259 A | 4/1990 | Packard | |
| 4,995,473 A | 2/1991 | Packard | |
| 5,111,904 A | 5/1992 | Packard | |
| 5,324,471 A | 6/1994 | Packard | |
| 5,380,182 A | 1/1995 | Packard | |
| 5,449,865 A | 9/1995 | Desnick et al. | |
| 5,592,946 A * | 1/1997 | Eddy | 600/528 |
| 5,686,706 A * | 11/1997 | Wurzburger | 181/131 |
| D395,509 S | 6/1998 | Packard et al. | |
| D403,465 S | 12/1998 | Zhuo | |
| D410,285 S | 5/1999 | Packard et al. | |
| 5,921,941 A | 7/1999 | Longobardo et al. | |
| 5,945,640 A | 8/1999 | Rossini et al. | |
| 5,949,032 A * | 9/1999 | Wurzburger | 181/131 |
| 6,006,856 A * | 12/1999 | Skubal et al. | 181/131 |
| 6,009,971 A * | 1/2000 | Weidman et al. | 181/131 |
| 6,050,950 A | 4/2000 | Mohler et al. | |
| D432,238 S | 10/2000 | Packard et al. | |
| 6,186,957 B1 * | 2/2001 | Milam | 600/528 |
| 6,324,289 B2 | 11/2001 | Orten | |
| 6,438,238 B1 | 8/2002 | Callahan | |
| 6,520,281 B1 | 2/2003 | Deslauriers et al. | |
| 6,575,917 B2 * | 6/2003 | Giroux et al. | 600/528 |
| 6,689,100 B2 | 2/2004 | Connelly et al. | |
| 6,725,966 B2 | 4/2004 | Drummond | |
| 6,966,400 B1 | 11/2005 | Rollins et al. | |
| 7,424,929 B1 * | 9/2008 | Martinez | 181/131 |
| 2001/0042656 A1 | 11/2001 | Deslauriers | |
| 2003/0201138 A1 * | 10/2003 | Drummond | 181/131 |
| 2004/0091678 A1 | 5/2004 | Jordan | |
| 2006/0018487 A1 * | 1/2006 | Smith | 381/67 |
| 2006/0227979 A1 * | 10/2006 | Chen | 381/67 |
| 2008/0089527 A1 * | 4/2008 | Shou | 381/67 |
| 2008/0137876 A1 * | 6/2008 | Kassal et al. | 381/67 |
| 2008/0230303 A1 * | 9/2008 | Weidman | 181/131 |

FOREIGN PATENT DOCUMENTS

WO  WO 2004/002191 A1  12/2003

* cited by examiner

STETHOSCOPE WITH FRICTIONAL NOISE REDUCTION

CROSS REFERENCE TO RELATED APPLICATIONS

This application is a national stage filing under 35 U.S.C. 371 of PCT/US2005/046520, filed Dec. 21, 2005, which claims priority to U.S. Provisional Application Ser. No. 60/640,497, filed Dec. 30, 2004, the disclosure of which is incorporated by reference in its/their entirety herein.

The present invention relates to means for reducing frictional noise associated with the sound receiving member of a stethoscope.

BACKGROUND

The stethoscope is a medical device for auscultation, i.e. listening to internal sounds in the human body. It is most often used to listen to heart and lung sounds, though it is also used to listen to the intestines and to the blood flow in both arteries and veins. Since its invention in 1819, the stethoscope has been used to listen to sounds within the human body as an aid in the diagnosis of certain diseases or health conditions. Prior to the invention of the stethoscope, a doctor listened to sounds from within the body by placing an ear against the patient's chest or elsewhere next to the patient's body.

Conventional stethoscopes include a sound receiving member (or chestpiece) which is configured for placement against the surface of a patient's skin to capture internal body sounds such as those emanating from the heart, lungs, blood vessels or the like. Traditionally, there have been two types of sound receiving members provided with conventional stethoscopes, the bell type and the diaphragm type. The bell type of sound receiving member is typically used to pick up low-pitched sounds while the diaphragm type picks up high-pitched sounds. Doctors may sometimes use a stethoscope having a combination bell/diaphragm sound receiving member. The diaphragm sound receiving member includes a membrane, or diaphragm, that selectively vibrates to sounds (e.g., a heart sound) generated within a certain frequency range from within the body to thereby amplify those sounds. Sound entering the bell type sound receiving member or the diaphragm sound receiving member is transmitted through tubing connected to a headset having a pair of earpieces configured to fit within the ears of the physician, nurse or other trained healthcare professional.

While stethoscopes employing diaphragm sound receiving members have been effective in the amplification of certain sound frequencies in the body, they have not been completely effective in reducing the level of "noise" entering the contact piece of the stethoscope. Sources of unwanted noise include frictional noises, for example. In one aspect, frictional noise arises as a result of friction between the sound receiving member of and the skin or clothing on a patient's body to which the sound receiving member is applied. Other sources of frictional noise can also include the friction between the physician's hands or fingers as he/she grasps the sound receiving member, or the friction between the hands of the physician and the tubing or other portions of the stethoscope.

The more recent development of electronic stethoscopes have utilized designs which incorporate a transducer as a sound receiving member to transform sound waves into an electrical signal. The transducer picks up the incoming sound and transmits it to signal conditioning circuits such as amplifiers or electronic filters which send the conditioned signal to speakers located in the earpieces of the stethoscope. While electronic stethoscopes can greatly amplify body sounds (e.g., the heartbeat), they also amplify the unwanted frictional noise arising as a result of the contact between the transducer (or a surface associated with the transducer) and the skin or clothing of a patient. These unwanted sounds can obscure the sounds of interest. In some cases, unwanted sounds can be amplified to an intensity that can cause discomfort to the user of the stethoscope.

The presence of frictional noise during auscultation can obscure certain sounds completely or at least diminish the ability of the physician to detect clinically significant sounds. Consequently, there is a need to provide a stethoscope or an improvement or modification of a stethoscope that is effective in reducing the level of frictional noise heard by the user.

SUMMARY

In an embodiment of the present invention, the invention provides a stethoscope, comprising: a sound receiving member for receiving sounds, the sound receiving member capable of transmitting sound received thereby; a head set coupled to the sound receiving member to receive sound transmitted by the sound receiving member; means for reducing frictional noise, said means associated with the sound receiving member to reduce noise caused by relative movement between a surface and the sound receiving member of the chestpiece in contact with the surface.

As used herein, "low friction material" refers to materials having a kinetic coefficient of friction of less than about 0.35 as measured according to ASTM D 1894 ("Standard Test Method for Static and Kinetic Coefficients of Friction of Plastic Film and Sheeting").

"Sound receiving member" is used interchangeably herein with "chestpiece."

The various features and details of the invention will be described to those of ordinary skill in the art in the context of the embodiments set forth in remainder of the disclosure including the Detailed Description taken together with the various Figures and the Examples.

BRIEF DESCRIPTION OF THE DRAWINGS

In describing embodiments of the invention, reference is made to the various Figures in which features of the embodiments are designated with reference numerals with like reference numerals generally indicating like structure, and wherein.

DETAILED DESCRIPTION

Figure 1:
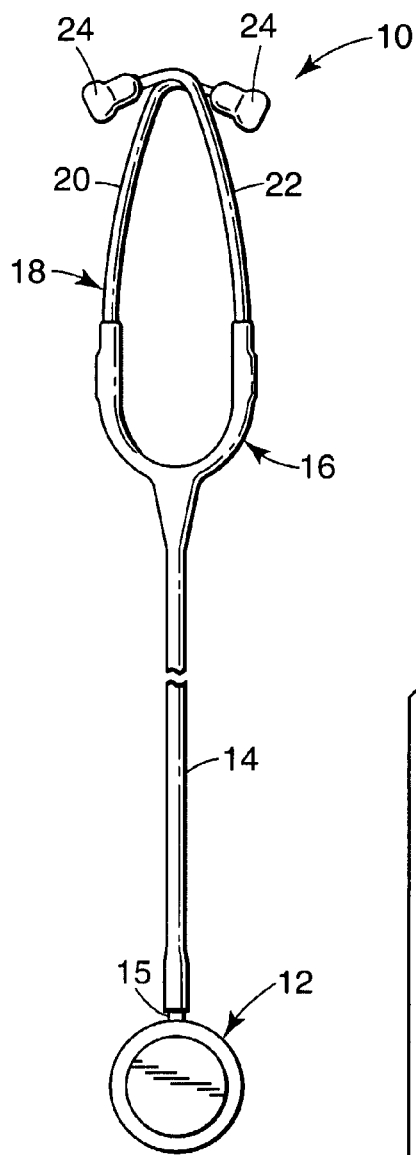
FIG. 1 is a perspective view of a stethoscope.

The present invention provides a means for reducing frictional noise in a stethoscope which can be applied to conventional mechanical or acoustical stethoscopes as well as electronic stethoscopes to reduce the level of frictional noise resulting from friction generated between the sound receiving member and the skin or clothing of a patient. Means for reducing frictional noise can be applied to the outer housing of the chestpiece to reduce frictional noise arising as a result of handling the housing of the sound receiving member. Additionally, means for reducing frictional noise can be applied to other areas of the stethoscope to reduce friction and noise resulting therefrom as a result of the handling of associated tubing on the stethoscope or other portions of the stethoscope. While specific constructions of stethoscopes are described in the context of describing various embodiments of the invention, it will be appreciated that the means for the reduction of frictional noise may be adapted to fit stethoscopes constructions not specifically described herein. The present invention is not to be construed as limited to any specific stethoscope construction.

In its more general aspects, the invention provides a stethoscope having a sound receiving member or chestpiece capable of transmitting sound received thereby; a head set acoustically coupled to the sound receiving member to receive sound transmitted by the sound receiving member; and means for reducing frictional noise, the means associated with the sound receiving member to reduce noise caused by contact between a surface and the sound receiving member. While the means for reducing frictional noise is at least to reduce noise caused by contact between a surface and the sound receiving member, the means may also be associated with other surfaces of the stethoscope such as an outer surface of the sound receiving member or the surface of the tubing. The means for reducing frictional noise will typically comprise one or more materials that, in some embodiments, is applied to a surface of the stethoscope, typically an external surface. Films, membranes, sheets, and coatings of suitable materials (as described herein) are exemplary of such means for reducing frictional noise. In some embodiments, means for reducing frictional noise can comprise a mixture of materials formed into a single film, sheet or membrane. In some embodiments, multiple layers of materials can be used. Additionally, means for reducing frictional noise can also be provided as stethoscope components comprising low friction materials admixed into or with other conventional materials or the low friction materials can be impregnated into other materials. For example, the means for reducing frictional noise can be provided as a diaphragm comprised of low friction materials blended into more standard materials used in the manufacture of a diaphragm.

In some embodiments, the invention is suitable for use in conjunction with mechanical stethoscopes such as those described, for example, in U.S. Pat. No. 3,276,536 (Littmann), U.S. Pat. No. 4,995,473 (Packard), U.S. Pat. No. 5,945,640 (Rossini et al.), U.S. Pat. No. 6,725,966 (Drummond), the disclosures of which are incorporated herein by reference thereto.

Referring to the various drawings, FIG. 1 is a perspective view of a stethoscope 10 suitable for use in one or more embodiments of the invention. The stethoscope 10 includes a sound receiving member or chestpiece 12 connected to tubing 14 which divides at yoke 16 into a headset 18 having dual sound transmitting tubes 20 and 22 terminating in ear tips 24. The chestpiece 12 of this embodiment includes two independent sound receiving cavities described in further detail below. The lower end 15 of the tubing 14 is adapted to be coupled to a stem fitting extending from the chestpiece 12. In some embodiments, the fitting may utilize an indexing detent as taught in U.S. Pat. No. 4,770,270 (Grimm), the entire disclosure of which is incorporated by reference herein. In some embodiments the tubing 14 can be prepared in accordance with the teachings of U.S. Pat. Nos. 5,111,904; 5,380,182; and 5,324,471, all to Packard et al., the entire disclosures of which are incorporated herein by reference thereto.

Ear tips 24 are sized and shaped to engage the surfaces of the user's ears. The ear tips 24 may be made from any of a variety of designs or constructions. In some embodiments, the ear tips 24 comprise the soft ear tips disclosed in U.S. Pat. No. 4,852,684 (Packard); U.S. Pat. No. 4,913,259 (Packard); and U.S. Pat. No. 5,449,865 (Desnick et al.), the entire disclosures of which are incorporated herein by reference thereto.

Figure 2:
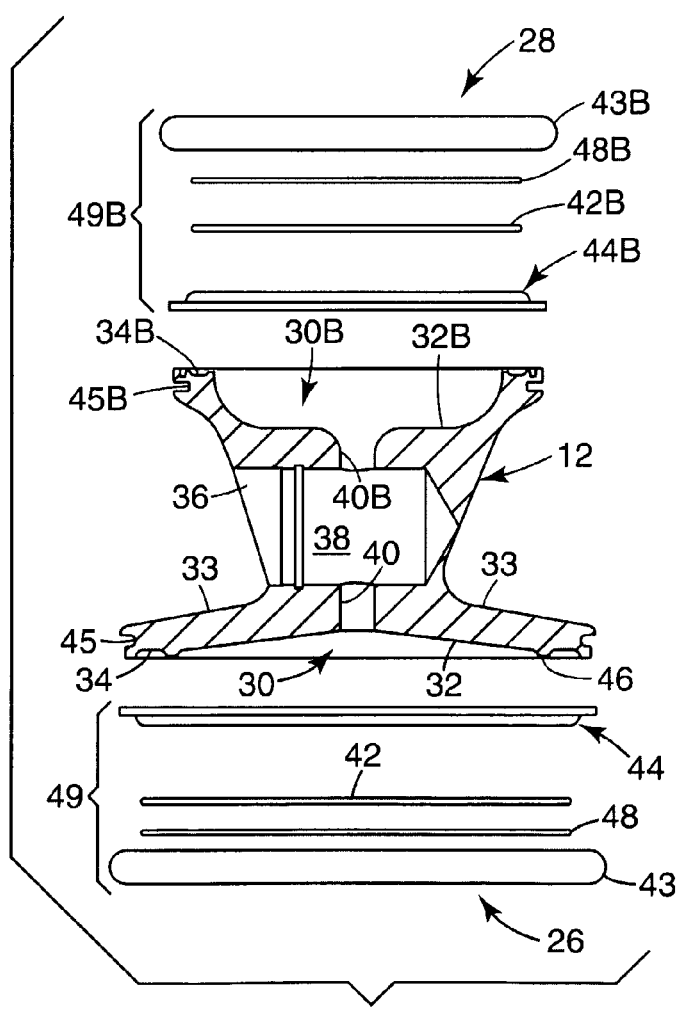
FIG. 2 is an exploded view of a side elevation, in cross section, of the sound receiving member of the stethoscope of FIG. 1 and constructed according to an embodiment of the invention.

Referring to FIG. 2, an enlarged side view of a chestpiece 12 suitable for use in the invention is shown in cross section. The chestpiece 12 is dual-sided with a first sound collecting side 26 and a second sound collecting side 28. In some embodiments, the first sound collecting side 26 can be sized and shaped to collect sounds from adult patients while the second sound collecting side 28 can be sized and shaped to afford sufficient surface contact to collect sound from pediatric patients or from thinner adult patients. The second sound collecting side 28 is smaller in diameter than the first sound collecting side 26.

As shown, the first sound collecting side 26 includes a first recess 30 with an innermost central portion 32, an outer rim portion 34, and an acoustic channel comprised of first portion 36, second portion 38, and third portion 40 communicating with the central portion 32 of first recess 30. The first portion 36 of the acoustical channel can be coupled to a stem fitting (not shown) extending from the first portion and dimensioned to fit within the lower end 15 of the tubing 14 (FIG. 1). As mentioned, the stem fitting may utilize an indexing detent. A first diaphragm 42 is also located on the first sound collecting side 26. The first diaphragm 42 includes a peripheral edge that can, in some embodiments, have a predetermined surface contour and which overlays at least a portion of the first recess 30. The first diaphragm 42 is associated with the outer rim portion 34 of the first recess 30.

A first suspension member 44 is provided on the first sound collecting side 26 between the outer rim portion 34 of the first recess 30 and the peripheral edge portion of the first diaphragm 42. The suspension member 44 is constructed to have substantially the same diameter as the first diaphragm 42 and interacts with the peripheral edge portion of the first diaphragm 42 when the suspension member 44 and the first diaphragm are affixed to the outer rim portion 34 of the first recess 30. The suspension member 44 provides a first acoustical stiffness for the first diaphragm 42 and allows movement or displacement of the first diaphragm 42 in a direction generally perpendicular to surface of the diaphragm. A lip 46 on the first sound collecting side 26 provides an innermost boundary between the rim portion 34 and the central portion 32 of the first recess 30. The lip 46 is sized and shaped to be contacted by the first suspension member 44.

In some embodiments, the first sound collecting side 26 of the chestpiece 12 can be constructed to permit the transmission of low frequency sounds while also attenuating high frequency sounds. In such a construction, the first diaphragm 42 is in the aforementioned position and the first suspension member 44 can be positioned against the rim portion 38. However, by positioning the chestpiece 10 against the skin or clothing of a patient and modifying the manual pressure exerted against the chestpiece, a physician can effectively reposition the first diaphragm 42 to be more closely adjacent the acoustic channel 40 within the first recess 30. When the first diaphragm 42 is in such an altered or innermost position, the acoustical stiffness of the first diaphragm 42 will be significantly higher than in the previously described position, and the first sound collecting side 26 of the chestpiece 12 can pass high frequency sounds while attenuating or blocking low frequency sounds.

Means for reducing frictional noise is provided to reduce the level of noise entering the stethoscope and attributable to the frictional contact between a surface and the diaphragm assembly 49. In auscultation, means for reducing frictional noise is intended to reduce the frictional noise resulting from contact between portions of the diaphragm assembly 49 of chestpiece 12 and the skin or clothing of a patient. In the present embodiment, the means for reducing frictional noise is provided in the form of a cover over the outermost surface of the first diaphragm 42. In the embodiment shown in FIG. 2, the means for reducing frictional noise is provided in the form of a membrane, sheet or film 48 comprised of a low friction material. The film 48 is applied to the first diaphragm 42 in a manner that positions the film 48 as the outermost surface of the first sound collecting side 26 on chestpiece 12. Accordingly, when the chestpiece 12 is used in the examination of a patient, the film 48 is placed against or in contact with the skin or outer clothing of the patient while the physician, nurse or other healthcare worker listen to heart sounds, lung sounds, or the like. The film 48 will be constructed from a low friction material to thereby reduce frictional noises generated when the chestpiece 12 is slid along the surface of the patient's skin or over the patient's outer clothing.

In some embodiments, the means for reducing frictional noise is applied to other parts of the chestpiece 12 as well as to other parts of the stethoscope 10. In some embodiments, means for reducing frictional noise can be applied to the outer surface 33 of a first recess 30 on the chestpiece 12 to dampen frictional noises resulting from movement of the physician's hands or fingers while manipulating the chestpiece 12 during the examination of a patient. In some embodiments, means for reducing frictional noise is applied to the tubing 14 (FIG. 1) to thereby dampen frictional noise resulting from contact between the tubing 14 and the physician's hands or fingers or between the tubing 14 and any other surface. It will be appreciated that the means for reducing frictional noise can be applied to any of the individual described parts of the stethoscope 10 as well as to any combination of parts. For example, some embodiments of the invention will include means for reducing frictional noise associated only with the diaphragm (e.g., diaphragm 42) while other embodiments will include means for reducing frictional noise associated with the diaphragm as well as the tubing and/or the outer surface 33 of the first recess 30.

Means for reducing frictional noise can comprise one or more materials that can be affixed to or otherwise associated with the chestpiece or other portions of a stethoscope. The means for reducing frictional noise can comprise any of a variety of low friction materials which may be applied to a stethoscope by any of a variety of methods. Specific materials suitable for use as means for reducing frictional noise include, without limitation, polytetrafluoroethylene ("PTFE"), polyurethane, polyethylene, parylene, polyester, polypropylene, other polymeric materials, fabrics, metals and combinations of two or more of the foregoing.

In some embodiments, the means for reducing frictional noise is provided in the form of a film, membrane, sheet, coating or the like which is affixed in some manner over the outer surface of at least a portion of the stethoscope. For example, the film, membrane, sheet, coating or the like can be adhesively affixed to the diaphragm of a mechanical stethoscope or to the rim surrounding of a standard bell mode. In some embodiments, the film, membrane, sheet, coating or the like can be provided in the form of a tape wherein the backing of the tape comprises a low friction film, membrane, sheet, or coating with an adhesive (e.g., a pressure sensitive adhesive) coated on a major surface of the backing to facilitate the attachment of tape to a portion of the stethoscope such as the diaphragm or other portions likely to contact the skin or clothing of a patient during auscultation, for example. Commercial materials suitable for use as a means for reducing frictional noise can include materials such as 3M Teflon Tape 5490 and 5425, for example, commercially available from 3M Company of St. Paul, Minn. Such tapes can be adhered to the chestpiece diaphragm and hand grip area. Another commercial material suitable for use as a means for the reduction of frictional noise is the film available under the trade designation "3M Scotchgard Paint Protection Film," also available from the 3M Company. This film can also provide scratch and chip protection for the housing or outer chestpiece areas.

In some embodiments, the film, membrane, sheet, or coating can be applied to a portion of the stethoscope in a melted or molten state and thereafter solidified (e.g., upon cooling). In some embodiments, the film, membrane, sheet, or coating can comprise a material that is sprayed onto the stethoscope and thereafter allowed to dry, cure, harden, or otherwise become affixed to the surface to which it is applied.

In some embodiments, means for reducing frictional noise can comprise a mixture of materials formed into a single film, sheet or membrane. In some embodiments, multiple layers of materials can be used. In other embodiments, means for reducing frictional noise can also be provided as stethoscope components comprising low friction materials admixed into or with other materials or the low friction materials can be impregnated into other materials. For example, the means for reducing frictional noise can be provided as a diaphragm comprised of low friction materials blended into more standard materials used in the manufacture of a diaphragm. Combinations of two or more of the foregoing constructions can also be used.

Retaining collar 43 is provided to retain the first diaphragm 42 in position suspended across first recess 30 and on the outermost surface of the diaphragm 42. The collar 43 is generally horseshoe-shaped in cross-section and is configured to retain the peripheral edge portions of first diaphragm 42 and the first suspension member 44 to the rim portion 34 of the first recess 30. The collar 43 nests within notch 45 to secure the collar 43 in position on the chestpiece 12. The retaining collar may comprise any of a variety of materials such as, for example, elastomeric polyurethanes, silicone rubbers, thermoplastic polymers, neoprene rubber, latex materials and the like. One suitable material for the collar 43 is that know under the trade designation "Bay Silicone LSR 2540," commercially available from Accusil, Inc., Merrillville, Ind.

In some embodiments, retaining collar 43 or a portion of retaining collar 43 will be constructed so that the collar 43, when positioned on the chestpiece as described herein, will contact the skin or clothing of a patient when the stethoscope is used in auscultation. In those embodiments, the collar 43 will typically be manufactured to include means for reducing frictional noise along at least a portion of the collar's surface. In some embodiments, the collar 43 can be made of the same low friction material as film, sheet or membrane 48. In some embodiments, the collar 43 can be made of materials dissimilar to those used for the film 48 but can include an additional layer of low friction material applied over a portion of the surface of collar 43. In other embodiments, the collar 43 can comprise a mixture of low friction material(s) admixed into the formulation for the collar, or low friction materials can be impregnated into the collar 43. Combinations and variations of the foregoing constructions can also be used.

In some embodiments, the collar 43 and first diaphragm 42 may be formed as an integral member during fabrication.

In some embodiments, the diaphragm 42 and suspension member 44 may be formed from a single sheet or film of material.

In embodiments where the collar 43 is air-impervious, it may be desirable to provide the diaphragm 42 and film 48 with a small hole therein to facilitate movement of the diaphragm and permit the movement of air between the first recess 30 and the atmosphere surrounding the chestpiece 12.

In some embodiments, the stethoscope 10 can be provided with only one sound collecting side such as sound collecting side 26, described herein. In some embodiments, the stethoscope 10 can be provided without the diaphragm assembly 49. In other words, the sound collecting side can be provided in an open bell configuration. In such embodiments, rim portion 34 comprises the portion of the chestpiece that will contact the patient's skin or clothing during auscultation. A non-chill ring may be provided around the rim portion 34 to reduce the thermal conductivity of the rim, and a low friction material may be applied to the rim 34 or to the non-chill ring, if present. The application of the low friction material to the rim or to the non-chill ring will be as described herein.

Referring again to FIG. 2, second sound collecting side 28 of the chestpiece 12 will now be described wherein at least some of the reference numerals will be similar to the reference numerals used in the description of the first sound collecting side 26 but using the added designation "B."

The second sound collecting side 28 has a second recess 30B with an innermost central portion 32B, an outer rim portion 34B, and an acoustic channel 40B communicating with the central portion 32B. The second sound collecting side 28 has a second diaphragm assembly 49B having diaphragm 42B with a peripheral edge portion and a predetermined surface contour overlying at least a portion of second recess 30B. The second diaphragm 42B is provided and is associated with the outer rim portion 34B of the second recess 30B.

Second diaphragm assembly 49B further includes second suspension member 44B located between the outer rim portion 34B of the second recess 30B and the peripheral edge portion of the second diaphragm 42B. The second suspension member 44B is positioned between the second diaphragm 42B and the outer rim portion 34B of the second recess 30B. A lip 46B, together with the central portion 32B of the second recess 30B, provides a shallow recess within the second recess 30B. The second suspension member 44B allows movement of the second diaphragm 42B in a direction generally perpendicular to the plane of the second diaphragm 42B and substantially in the same manner as described previously with respect to the first diaphragm 42.

In some embodiments, the second sound collecting side 28 of the chestpiece 12 will pass low frequency sounds while attenuating high frequency sounds when the second diaphragm 42B is in the outermost position with respect to the second suspension means 44B. By positioning the second sound collecting side 28 of the chestpiece 12 against the skin of a patient and modifying the manual pressure exerted against the chestpiece 12, a physician can reposition the second diaphragm 42B to be more closely adjacent the acoustic channel 40B within the second recess 30B. When the second diaphragm 42B is in such an innermost position, the acoustical stiffness of the second diaphragm 42B will be significantly higher than in the previously described position, and the second sound collecting side 28 will typically pass high frequency sounds while attenuating or blocking low frequency sounds.

Means for reducing frictional noise is provided to cover the outermost surface of the second diaphragm 42B. In some embodiments such as that shown in FIG. 2, the means for reducing frictional noise is provided in the form of a sheet or film 48B comprised of a low friction material. When the film 48B is applied to the second diaphragm 42B, film 48B is applied in a manner that provides the film 48B as the outermost surface of the second sound collecting side 28 on chestpiece 12. When the chestpiece 12 is used in the examination of a patient, the film 48B will interact with the skin or outer clothing of the patient while the physician, nurse or other healthcare worker listens to heart sounds, lung sounds, or the like. Moreover, the film 48B will be constructed from a material that reduces the level of frictional noise entering the stethoscope through the second sound collecting side such as the sounds generated by the friction created when sliding the chestpiece 12 along the surface of the patient's skin or over the patient's outer clothing.

In some embodiments, such as that depicted in FIG. 2, the size and shape of the first sound collecting side 26 is different than the size and shape of the second sound collecting side 28.

In some embodiments, the stethoscope 10 may be provided with only one sound collecting side such as sound collecting side 26, as described herein. Alternatively, the stethoscope may be provided with a single sound collecting side resembling sound collecting side 28. In some embodiments, the second sound collecting side 28 can be provided without the diaphragm assembly 49B. In other words, the sound collecting side 28 can be provided in an open bell configuration. In such embodiments, rim portion 34B comprises the portion of the chestpiece that will contact the patient's skin or clothing during auscultation. A non-chill ring (not shown) may be provided around the rim portion 34B to reduce the thermal conductivity of the rim, and a low friction material may be applied to the rim 34B or to the non-chill ring, if present. The application of the low friction material to the rim or to the non-chill ring can be accomplished in a known manner, according to methods described herein.

The first and second diaphragms 42 and 42B may comprise the same or different materials and can be constructed from any of a variety of suitable materials such as, for example, plastics such as polyester, fiberglass-reinforced plastics and polystyrene and metals such as stainless steel. In some embodiments, the thickness of diaphragm 42B can range from about 5 to 20 mils (0.013 to 0.051 centimeters).

In some embodiments, the second diaphragm 42B comprises a 0.01 mil-thick epoxy resin-fiberglass laminate such as those commercially available from InsulFab of Franklin, N.H.

Retaining collar 43B is provided to retain the second diaphragm 42B in position suspended across second recess 30B. The collar 43B is generally horseshoe-shaped in cross-section and is configured to attach the peripheral edge portions of second diaphragm 42B and the second suspension member 44B to the rim portion 34B of the second recess 30B. The collar 43B nests within notch 45B to secure the collar 43B in position on the chestpiece 12. The retaining collar 43B may comprise any of a variety of materials including those mentioned previously with respect to the first collar 43.

In some embodiments, retaining collar 43B or a portion of retaining collar 43B will be constructed so that the collar 43B, when positioned on the chestpiece 12 as described herein, will contact the skin or clothing of a patient when the stethoscope is used in auscultation. In those embodiments, the collar 43B will typically be manufactured to include means for reducing frictional noise along at least a portion of the collar's surface. In some embodiments, the collar 43B can be made of the same low friction material as film, sheet or membrane 48B. In some embodiments, the collar 43B can be made of materials dissimilar to those used for the film 48B but can include an additional layer of low friction material applied over a portion of the surface of collar 43B. In other embodiments, the collar 43B can comprise a mixture of low friction material(s) admixed into the formulation for the collar, or low friction materials can be impregnated into the collar 43B. Combinations and variations of the foregoing constructions can also be used.

In some embodiments, the collar 43B and second diaphragm 42B may be formed as an integral member during fabrication.

In some embodiments, the diaphragm 42B and suspension member 44B may be formed from a single sheet or film of material.

In embodiments where the collar 43B is air-impervious, it may be desirable to provide the diaphragm 42B with a small hole therein to facilitate movement of the diaphragm and permit the movement of air between the second recess 30B and the atmosphere surrounding the chestpiece 12.

While the foregoing embodiment of a stethoscope constitutes an embodiment of the present invention, it will be appreciated that the present invention is applicable to any of a variety of stethoscope constructions having at least one sound collecting portion as a part thereof.

In some embodiments, the invention is suitable for use in conjunction with electronic stethoscopes such as that described in WO 2004/002191 A1. While frictional noise in a mechanical stethoscope can be troublesome, such frictional noise can be a more significant problem in the use of an electronic stethoscope because electronic stethoscopes greatly amplify incoming sounds, including frictional noise.

Figure 3:
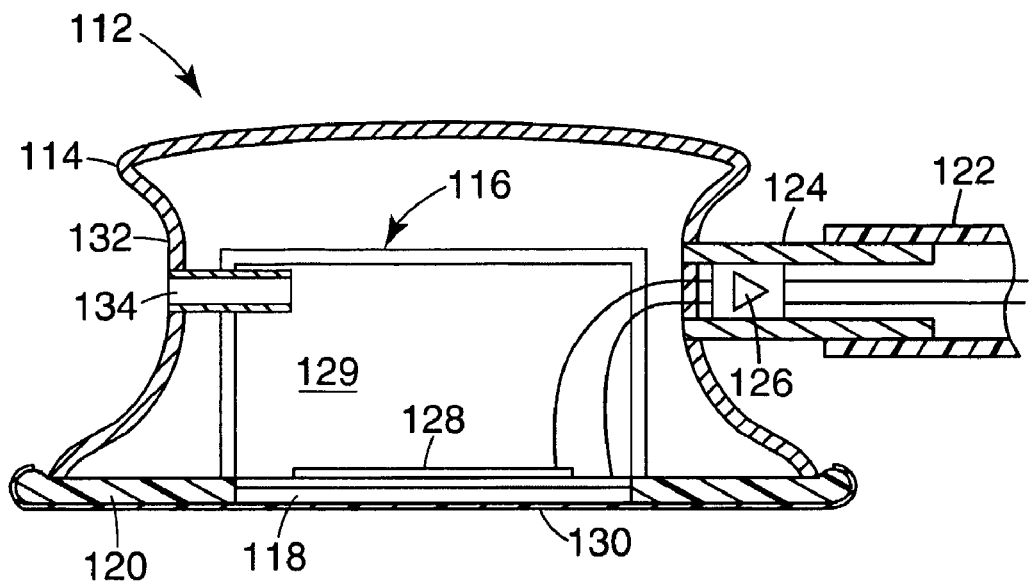
FIG. 3 is an elevated side view, in cross section, of the sound receiving member of an electronic stethoscope according to an embodiment of the invention.

Referring now to FIG. 3, a sound receiving member or chestpiece 112 from an electronic stethoscope is shown in cross section. The chestpiece 112 includes an outer housing 114 and an inner housing 116 holding a cover member 118 by its rim and creating a surround 120. Tubing 122 is affixed to a stem 124 of the chestpiece 112 providing a clamping arrangement for a signal lead and its electrostatic shielding. The stem 124 can hold a preamplifier and impedance converter 126. The diaphragm can be a transflexural piezoelectric laminate. However, other forms of electro-mechanical transducers can be used including microphones, for example. The electrode is deposited onto opposite sides of the thin sheet of piezoelectric material, which gives off a voltage when flexed. Or, the diaphragm can be a conventional diaphragm such as diaphragm 42 in FIG. 2, with a piezoelectric transducer 128 which is surface mounted. The diaphragm 118 is mounted flush with or approximately in the same plane as the outermost rim of the surrounding housing. Surround 120 is provided with a width to allow for close contact between the chestpiece 112 and the skin or the outer clothing of a patient. The housing 114 is closed to shield the rear of the diaphragm 118 from airborne sound and thus creating cavity 129 within the chestpiece 112.

Means for reducing frictional noise is provided to cover the outermost surface of the cover member 118. In some embodiments, such as that shown in FIG. 3, the means for reducing frictional noise is provided in the form of a sheet, membrane or film 130 comprised of a material having a low coefficient of friction, as previously described. The film 130 is applied over diaphragm 118 and serves as the outermost sound collecting surface on chestpiece 112. When the electronic chestpiece 112 is used in the examination of a patient, the film 130 will interact with the skin or outer clothing of the patient while the physician, nurse or other healthcare worker listen to heart sounds, lung sounds, or the like. The features and characteristics of the sheet or film 130 and the materials used to make such a film or sheet are as previously described herein.

In some embodiments, a port 134 (or an equivalent structure) may optionally be included in the chestpiece 112 so that the cavity 129 is in communication with and open to the surrounding atmosphere as taught, for example in the aforementioned patent application WO 2004/002191 A1.

Figure 4:
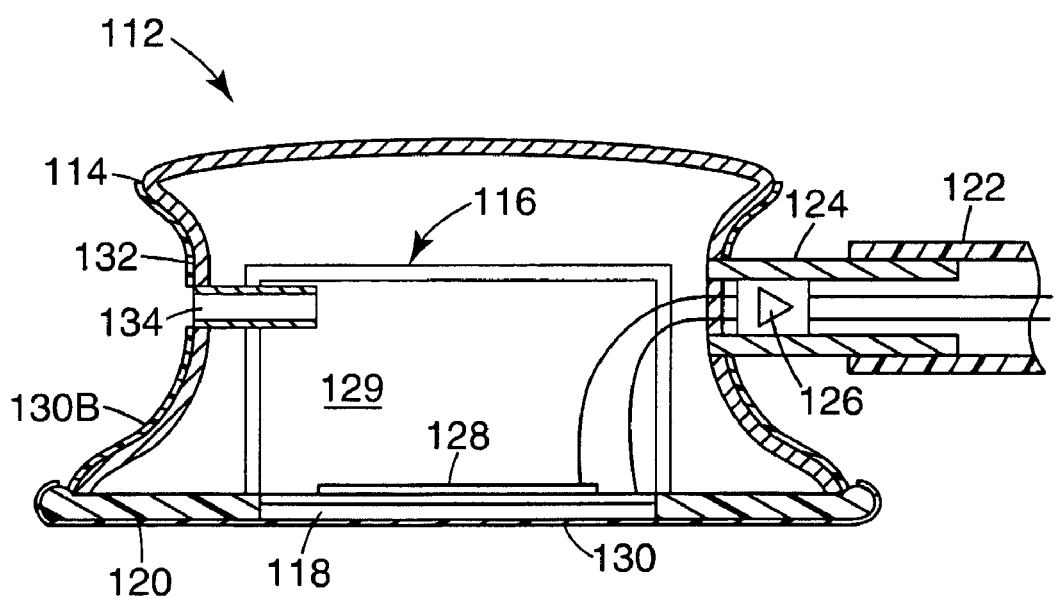
FIG. 4 is an elevated side view, in cross section, of the sound receiving member of an electronic stethoscope according to another embodiment of the invention.

In some embodiments, means for reducing frictional noise can be applied to other parts of the chestpiece 112. Referring now to FIG. 4, additional means for reducing frictional noise such as film, membrane or sheet 131B can be applied to the outer surface 132 of the housing 114 to dampen frictional noises resulting from movement of the physician's hands or fingers while grasping the chestpiece 112 during the examination of a patient. In some embodiments, additional means (not shown) for reducing frictional noise can be applied to the tubing 122 to dampen frictional noises resulting from the movement of the physician's hands or fingers while grasping the tubing 122 during the examination of a patient. As discussed previously, the foregoing applications of means for reducing frictional noise on the various portions of a stethoscope can be applied to any of the individual parts of an electronic stethoscope. For example, some embodiments of the invention will include means for reducing frictional noise associated only with the diaphragm while other embodiments will include means for reducing frictional noise associated with the diaphragm, the tubing and/or the outer surface 132 of the housing 114.

It will be appreciated that the foregoing description of an electronic stethoscope is not to be construed as limiting the scope of the invention. In general, means for reducing frictional noise may be applied to an electronic stethoscope to reduce the frictional noise received by the stethoscope's electronic circuitry. Typically, the means for reducing frictional noise will comprise the aforementioned membrane, sheet or film affixed or otherwise associated with the sound detection interface (e.g., piezoelectric element 128 and diaphragm 118) of the sound receiving member. Constructions for an electronic stethoscope other than those depicted in FIGS. 3 and 4 are contemplated as comprising, at a minimum, a sound receiving member having a transducer, microphone, piezoelectric element or the like associated with a surface that is suitable for placement against a patient's skin or clothing. Housing or the like placed around the piezoelectric element will typically be for the protection of the electronic components and not for the enhancement of sound. Typically, the sound receiving member is coupled speakers that may be positioned within the ears of the doctor, nurse or healthcare worker. Coupling of the speakers and sound receiving member is accomplished with suitable electronic circuitry, as known by those skilled in the art.

The means for the reduction of frictional noise of the present invention lowers the coefficient of friction for the surface of the stethoscope. Frictional noise can arise as a result of slight movement of the stethoscope over a surface such as the skin or clothing of a medical patient, for example. A frictional noise frequency spectra over the frequency range of 10 to 1000 Hz, described further in the Examples herein, will exhibit a reduction in the overall frictional noise level for a stethoscope having a low friction material associated with the sound collecting surface thereof compared with the same stethoscope without such low friction material. Moreover, the reduction in frictional noise demonstrated by the use of the present invention is accomplished without reduction in sound quality.

While frictional noise can be significant for traditional acoustic or mechanical stethoscopes, frictional noise is a more significant problem for electronic stethoscopes. The electronic circuitry within an electronic stethoscope is configured to amplify the sounds detected by the stethoscope, including the frictional noise. As a consequence, some physicians prefer not to use electronic stethoscopes because the frictional noise level is too great a distraction. The use of means for reducing frictional noise on an electronic stethoscope, according to the present invention, reduces the frictional noise levels without reducing the base signal.

In some embodiments, the means for reducing frictional noise over the frequency range from about 10 to about 1000 Hz is effective to reduce the average frictional noise level by about 3 dBA to about 5 dBA. In other embodiments, especially in electronic stethoscopes constructed with a chestpiece like those shown in FIGS. 3 and 4 and described herein, the means for reducing frictional noise over the frequency range from about 10 to about 1000 Hz is effective to reduce the average frictional noise level by about 17 dBA.

Additional features of the embodiments of the invention are illustrated in the following non-limiting Examples.

EXAMPLES

The invention is further illustrated by the following non-limiting examples.

Test Methods

Noise Measurements

Example stethoscopes were attached at the ear-piece end to a B&K Head and Torso Simulator (HATS) system available from Brüel & Kjær of Nærum (B&K), Denmark. The HATS system was controlled by hardware and software data acquisition systems, also available from B&K, under the trade name PULSE, and used according to the operating manual, "*PULSE—Getting Started: An Introduction to PULSE*". The software used was PULSE Version 9.0 Type 7700. The hardware was a 2-channel Type 3109 PULSE input/output generator module. Acoustic signals of various frequencies were generated using a sounder consisting of a speaker and a gel pad. The speaker was driven by an electrical signal generator. The sounder further consisted of a calibrated microphone, which was used to monitor the input to the sounder. The calibrated microphone inside the sounder was connected to the input of the PULSE generator module. The PULSE generator module output was connected to a TPA3001D1 audio amplifier available from Texas Instruments. The stethoscope chestpiece was fixed on the top of the sounder. A 2-channel fast fourier transform (FFT) analysis was performed with the following settings:

Generator Setup: Waveform=Swept Sine; Level=5 mV rms; Start-Stop Frequency=1 mHz-2.5 kHz; Sweep Rate=40 Hz/s; Sweep Mode=unidirectional.

FFT Analyzer Setup: Lines=800; Span=6.4 kHZ; Averaging Domain=Spectrum Averaging; Overlap=75%; Analysis mode=Baseband; Averaging mode=Linear; Average time=45 seconds.

In Situ Frictional Noise Generation Procedure

The chestpiece diaphragm of each example stethoscope was rubbed with gentle pressure against a human test subject in the chest area above the heart at a pace of approximately 2.5 cm (1 inch) per second. This procedure was repeated three times and the average value of the frictional sound intensity was recorded for each stethoscope type, with and without Teflon tape.

Comparative and Example Stethoscopes Tested for Frictional Noise

Frictional noise reduction was accomplished by applying 3M Teflon (PTFE) Film Tape 5425, available from 3M Company of St. Paul, Minn., to the chestpiece diaphragm. The frictional noise frequency spectra of example stethoscopes, with and without the Teflon tape applied at the surface of the diaphragm, was generated and measured according to the methods and equipment described above. The example stethoscopes were: Models 3000, Model 4000 and Cardiology III, all from 3M Company of St. Paul, Minn., under the Littmann Brand. The Model 3000 was an electronic stethoscope constructed with a chestpiece essentially as is described herein in conjunction with the chestpiece shown in FIG. 3. The Cardiology III was a mechanical scope. The Model 4000 was an electronic stethoscope utilizing a microphone to detect sound. The microphone is recessed within a chestpiece housing and did not contact the 3M Teflon Film used herein to reduce frictional noise. A second type of Teflon tape (3M Teflon (PTFE) Film Tape 5490) was also applied to the Model 3000 stethoscope. Results are shown in Table 1.

TABLE 1

| | Frequency (Hz) vs. Frictional Noise Levels (dBA) | | | | | | |
|---|---|---|---|---|---|---|---|
| | Model 3000 (dBA) | | | Model 4000 (dBA) | | Cardiology III (dBA) | |
| Frequency (Hz) | No Tape | with 3M 5425 tape | with 3M 5490 tape | No Tape | with 3M 5425 tape | No Tape | with 3M 5425 tape |
| 50.0 | 42.5 | 30.5 | 31.7 | 28.3 | 27.4 | 34.4 | 34.4 |
| 100.0 | 48.9 | 33.0 | 35.8 | 29.6 | 31.1 | 39.1 | 34.3 |
| 300.0 | 72.2 | 52.9 | 54.9 | 58.0 | 54.3 | 47.6 | 41.7 |
| 600.0 | 59.5 | 43.4 | 46.2 | 55.3 | 47.8 | 45.2 | 37.7 |
| 900.0 | 58.0 | 42.3 | 43.4 | 41.2 | 39.5 | 42.4 | 35.3 |

Figure 5:
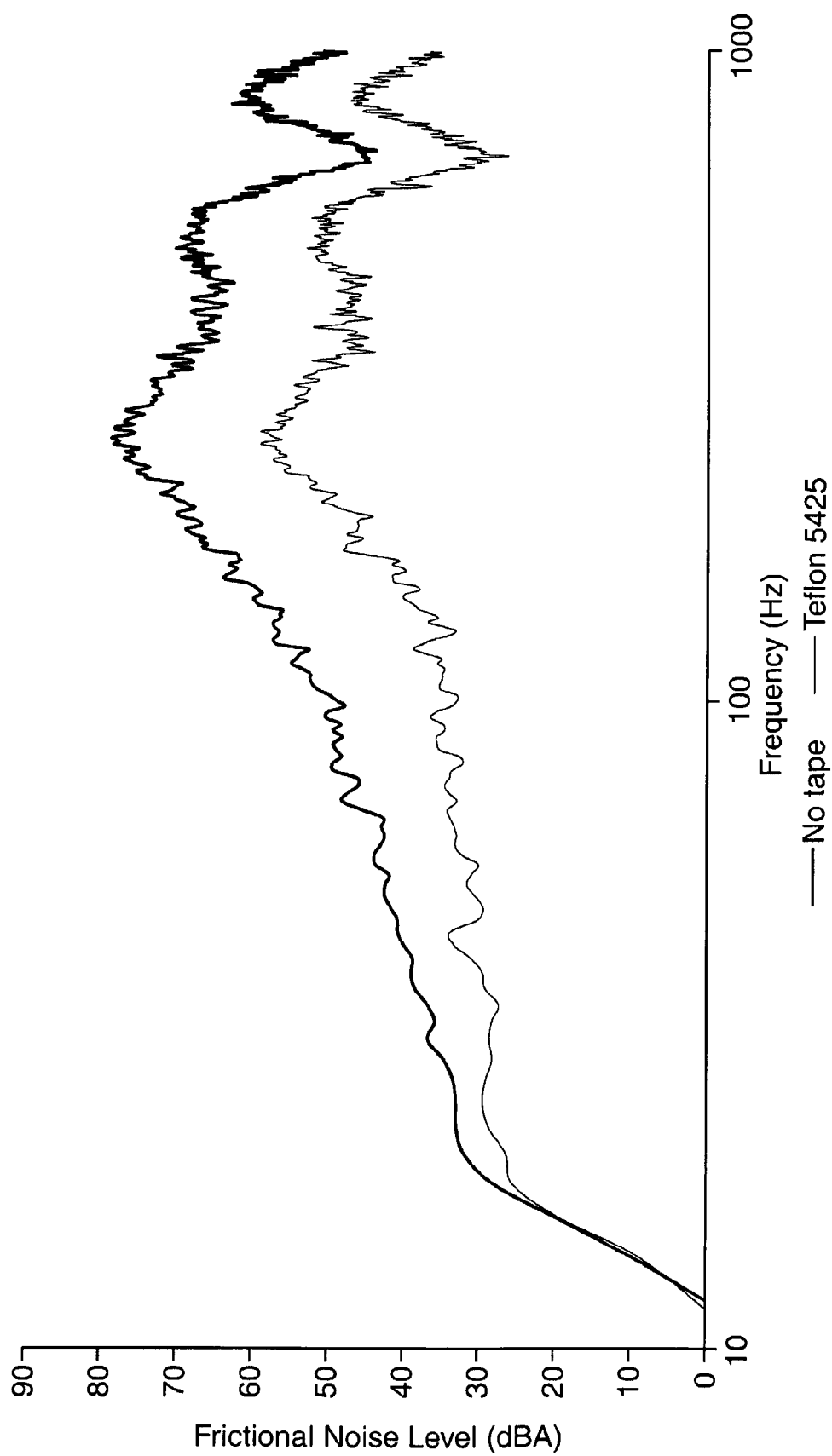
FIG. 5 is a comparative plot of the frictional noise level for a stethoscope across frequencies from 10 to 1000 Hz, showing data for the stethoscope with and without frictional noise reduction according to the present invention.

FIG. 5 also shows the frictional noise level for the Model 3000 stethoscope across frequencies from 10 to 1000 Hz, with and without the 5425 Teflon film tape. The data points for the first two columns under the Model 3000 heading in Table 1 are also taken from the same frequency spectra as FIG. 5.

Figure 6:
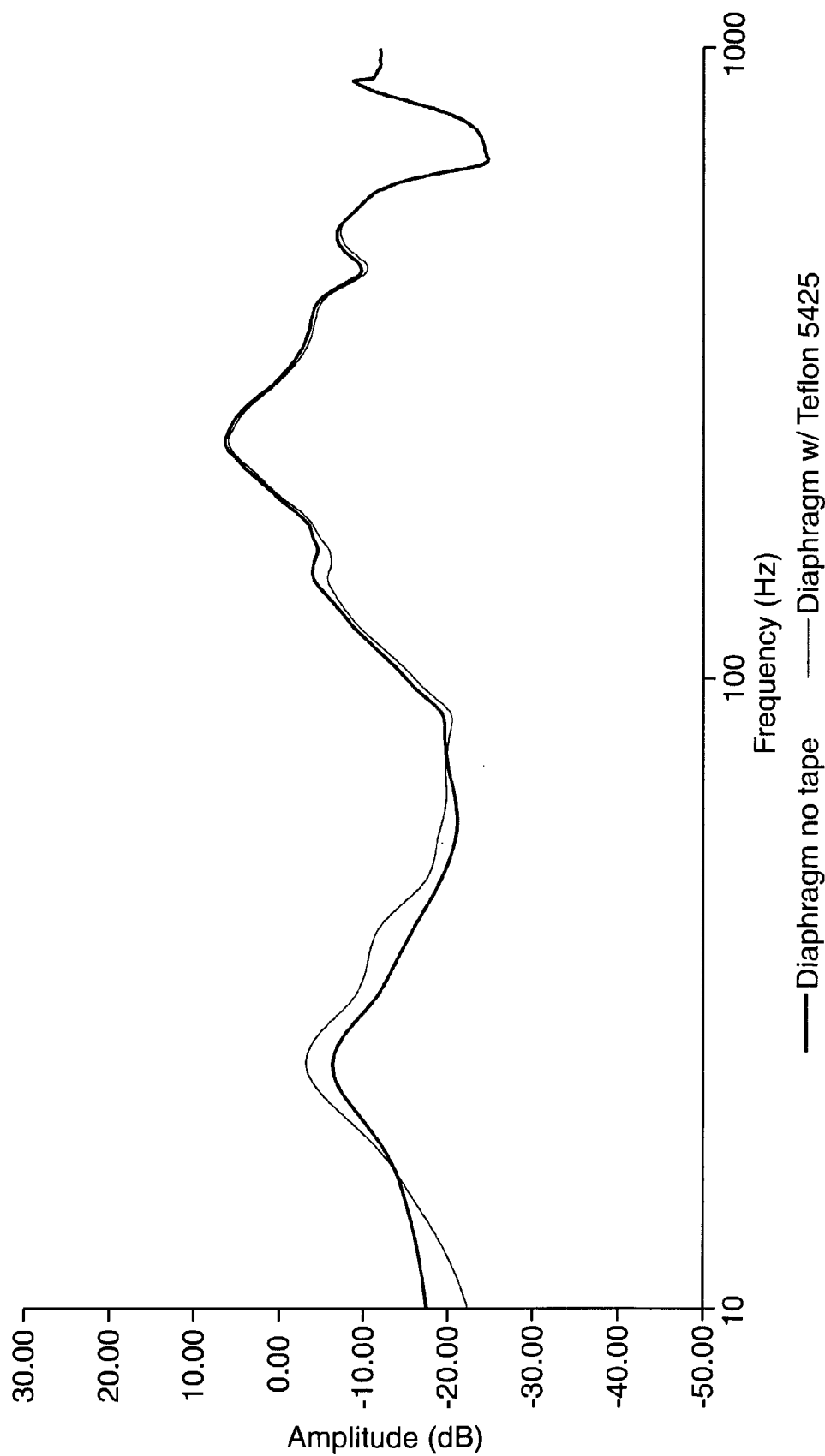
FIG. 6 is a comparative frequency response spectra for a sweep analysis of a stethoscope with and without frictional noise reduction according to the present invention and further described in the Examples herein.
Figure 7:
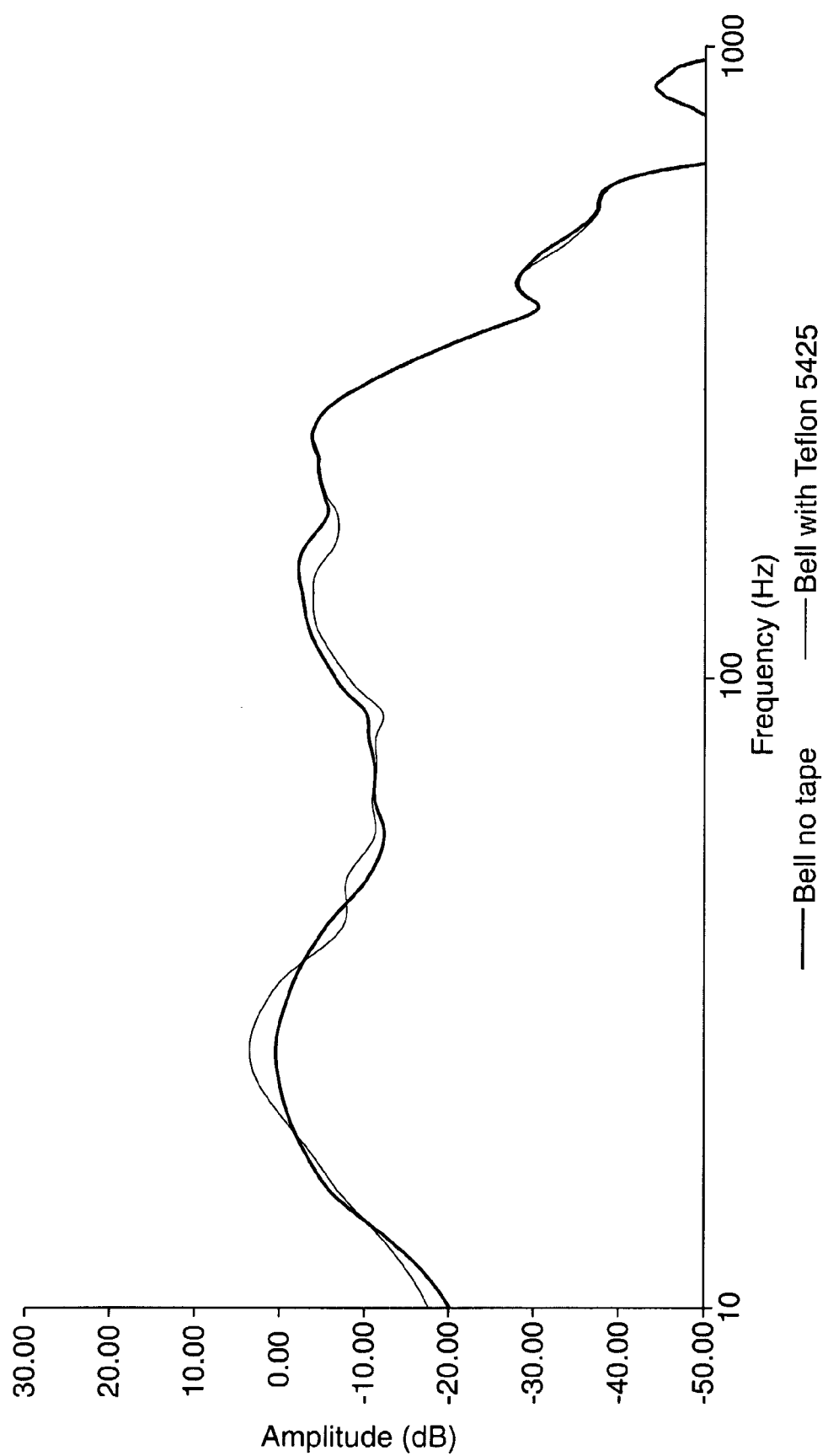
FIG. 7 is another comparative frequency response spectra for a sweep analysis of a stethoscope with and without frictional noise reduction according to the present invention and further described in the Examples herein.

FIGS. 6 and 7 show the frequency response spectra for a sweep analysis of the Model 3000 stethoscope with and without the 3M 5425 Teflon tape coating on the diaphragm for both the Diaphragm and Bell filter modes, respectively, using the B&K HATS equipment described above. These figures show that the frequency response (sound quality) of the stethoscope with the Teflon tape is not significantly different that the frequency response of the stethoscope without the Teflon tape.

The overall frictional noise levels of different stethoscopes with and without the 3M 5425 Teflon tape are shown in Table 2.

TABLE 2

| Overall Frictional Noise Levels (dBA) | | | | | |
|---|---|---|---|---|---|
| Model 3000 (dBA) | | Model 4000 (dBA) | | Cardiology III (dBA) | |
| No Tape | with 3M 5425 tape | No Tape | with 3M 5425 tape | No Tape | with 3M 5425 tape |
| 92.5 | 75.0 | 78.8 | 75.2 | 70.4 | 64.7 |

This data in Table 3 indicates that the frictional noise of an electronic stethoscope such as the Model 3000 can be lowered to the same level of noise as an acoustic stethoscope. Frictional noise of an acoustic stethoscope can also be improved.

While a preferred embodiment of the invention has been described, it will be understood that the invention is not to limited to the described embodiment. Changes or modifications may be made to the various features of the embodiment described herein without departing from the spirit and scope of the invention as set forth in the following claims.

What is claimed is:

1. A stethoscope, comprising:
   a sound receiving member comprising electronic components adapted to receive and transmit sounds;
   an outer surface at least partially defined by the sound receiving member; and
   means for reducing frictional noise, the means for reducing frictional noise comprising a low friction material and being coupled to at least a portion of the outer surface.

2. The stethoscope as defined in claim 1 wherein the sound receiving member further comprises an inner cavity and an opening from the outer surface to the inner cavity, wherein sound passing through the opening enters the inner cavity and the means for reducing frictional noise is associated with the opening.

3. The stethoscope as defined in claim 2, the sound receiving member further comprising a diaphragm positioned over the opening, the diaphragm having a first major surface facing into the inner cavity and a second major surface facing away from the inner cavity, the diaphragm constructed to pass sound waves of a first frequency range into the inner cavity, and wherein the means for reducing frictional noise is associated with the second major surface of the diaphragm.

4. The stethoscope as defined in claim 1 wherein the means for reducing frictional noise includes at least one of a film, a membrane, a sheet, a coating, a spray, and a collar.

5. The stethoscope as defined in claim 1 wherein the low friction material has a kinetic coefficient of friction of less than about 0.35 as measured according to ASTM D 1894-01.

6. The stethoscope of claim 1, wherein the low friction material includes at least one of polytetrafluoroethylene ("PTFE"), polyurethane, polyethylene, parylene, polyester, polypropylene, and a combination thereof.

7. The stethoscope of claim 1, wherein the sound receiving member includes an opening and a diaphragm positioned over the opening, and wherein the means for reducing frictional noise is coupled to the diaphragm.

8. The stethoscope of claim 1, further comprising a tape coupled to at least a portion of the outer surface, wherein the tape is at least partially formed of the means for reducing frictional noise.

9. The stethoscope of claim 1, further comprising:
   a head set coupled to the sound receiving member to receive sound transmitted by the sound receiving member; and
   tubing positioned to couple the head set to the sound receiving member;
   wherein the outer surface is at least partially defined by the sound receiving member and the tubing and wherein the means for reducing frictional noise is coupled to a portion of the outer surface defined by the sound receiving member and the tubing.

10. The stethoscope of clam 1, further comprising a head set electronically coupled to the sound receiving member to receive sound transmitted by the sound receiving member.

11. The stethoscope of clam 1, wherein the sound receiving member comprises an electronic component selected from the group consisting of a transducer, microphone, and piezo-electric element.

12. The stethoscope of clam 1, wherein the means for reducing frictional noise reduces the frictional noise levels without reducing the base signal.

13. The stethoscope of claim 1, wherein the means for reducing frictional noise over the frequency range from about 10 to about 1000 Hz is effective to reduce the average frictional noise level by at least about 3 dBA.

14. The stethoscope of clam 1, wherein the means for reducing frictional noise over the frequency range from about 10 to about 1000 Hz is effective to reduce the average frictional noise level by at least about 5 dBA.

15. The stethoscope of clam 1, wherein the means for reducing frictional noise over the frequency range from about 10 to about 1000 Hz is effective to reduce the average frictional noise level by about 17 dBA.

* * * * *

UNITED STATES PATENT AND TRADEMARK OFFICE
CERTIFICATE OF CORRECTION

| | | |
|---|---|---|
| PATENT NO. | : 7,806,226 B2 | Page 1 of 1 |
| APPLICATION NO. | : 11/722529 | |
| DATED | : October 5, 2010 | |
| INVENTOR(S) | : Thomas Edward Drummond | |

It is certified that error appears in the above-identified patent and that said Letters Patent is hereby corrected as shown below:

Column 14
Line 4, in claim 3, after "and" delete "wherein".
Line 35, in claim 10, delete "clam 1" and insert in place thereof -- claim 1 --.
Line 38, in claim 11, delete "clam 1" and insert in place thereof -- claim 1 --.
Line 42, in claim 12, delete "clam 1" and insert in place thereof -- claim 1 --.
Line 45, in claim 13, delete "clam 1" and insert in place thereof -- claim 1 --.
Line 49, in claim 14, delete "clam 1" and insert in place thereof -- claim 1 --.
Line 53, in claim 15, delete "clam 1" and insert in place thereof -- claim 1 --.

Signed and Sealed this
Twenty-ninth Day of March, 2011

David J. Kappos
*Director of the United States Patent and Trademark Office*